United States Patent
Neu et al.

(10) Patent No.: US 11,129,543 B2
(45) Date of Patent: Sep. 28, 2021

(54) SOFT TISSUE MATRIX CHARACTERIZATION USING STRETCHED EXPONENTIAL RELAXATION MODELING

(71) Applicants: The Regents of the University of Colorado, Denver, CO (US); Emory University, Atlanta, GA (US)

(72) Inventors: Corey P. Neu, Boulder, CO (US); Robert L. Wilson, Boulder, CO (US); David Reiter, Decatur, GA (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

(21) Appl. No.: 17/259,134

(22) PCT Filed: Jul. 8, 2019

(86) PCT No.: PCT/US2019/040845
§ 371 (c)(1),
(2) Date: Jan. 8, 2021

(87) PCT Pub. No.: WO2020/014145
PCT Pub. Date: Jan. 16, 2020

(65) Prior Publication Data
US 2021/0244307 A1  Aug. 12, 2021

Related U.S. Application Data

(60) Provisional application No. 62/695,603, filed on Jul. 9, 2018, provisional application No. 62/695,152, filed on Jul. 8, 2018.

(51) Int. Cl.
*A61B 5/00* (2006.01)
*A61B 5/055* (2006.01)
*A61B 5/0515* (2021.01)

(52) U.S. Cl.
CPC ............ *A61B 5/055* (2013.01); *A61B 5/0515* (2013.01); *A61B 5/4566* (2013.01); *A61B 5/742* (2013.01); *A61B 2560/02* (2013.01)

(58) Field of Classification Search
CPC ....... A61B 5/055; A61B 5/4566; A61B 5/742; A61B 5/0515; A61B 2560/02
See application file for complete search history.

(56) References Cited

U.S. PATENT DOCUMENTS 9,933,497 B2   3/2018  Aktiengesellschaft
2002/0188190 A1  12/2002  Kassai et al.
(Continued)

FOREIGN PATENT DOCUMENTS

WO  WO20200014145   9/2019
WO  WO20200014145   1/2020

*Primary Examiner* — Joel Lamprecht
(74) *Attorney, Agent, or Firm* — Michael M. McGaw; McGaw Law, P.C.

(57) ABSTRACT

A process for more sensitive characterization of tissue composition for generating a quantitative MRI (qMRI) map and corresponding delta analysis. Intervertebral disc degeneration (IVDD), resulting in the depletion of hydrophilic glycosaminoglycans (GAGs) located in the nucleus pulposus (NP), can lead to debilitating neck and back pain. Magnetic Resonance Imaging (MRI) is a promising means of IVD assessment due to the correlation between GAG content and MRI relaxation values. T1 and T2 relaxation data were obtained from healthy cervical IVDs, and relaxation data was modeled using both conventional and stretched exponential (SE) decays. Normalized histograms of the resultant quantitative MRI (qMRI) maps were fit with stable distributions. SE models fit relaxation behavior with lower error compared to monoexponential models, indicating anomalous relaxation behavior in healthy IVDs. SE model parameters T1 and T1 increased with IVD segment, while conventional monoexponential measures did not vary.

(Continued)

The improved model fit and correlation between both SE T1 and T1 with IVD level suggests these parameters are more sensitive biomarkers for detection of GAG content variation.

12 Claims, 13 Drawing Sheets

(56) References Cited

U.S. PATENT DOCUMENTS

| | | | |
|---|---|---|---|
| 2008/0039710 A1* | 2/2008 | Majumdar | G01R 33/00 |
| | | | 600/410 |
| 2011/0054299 A1 | 3/2011 | Ling et al. | |
| 2012/0286781 A1 | 11/2012 | Zijl et al. | |
| 2016/0081578 A1* | 3/2016 | Gazit | A61B 5/004 |
| | | | 600/410 |
| 2019/0307393 A1* | 10/2019 | Lotz | A61B 5/004 |

* cited by examiner

SOFT TISSUE MATRIX CHARACTERIZATION USING STRETCHED EXPONENTIAL RELAXATION MODELING

CROSS-REFERENCE TO RELATED APPLICATIONS

This application claims the benefit of U.S. Provisional Application No. 62/695,152, filed Jul. 8, 2018, and U.S. Provisional Application No. 62/695,603, filed Jul. 9, 2018.

STATEMENT OF GOVERNMENT INTEREST

This invention was made with government support under grant number AR066665, awarded by the National Institutes of Health. The government has certain rights in the invention.

FIELD OF INVENTION

This invention relates to magnetic resonance imaging. More specifically, this invention relates to methods of generating quantitative MRI maps for the assessment of intervertebral disc degeneration.

BACKGROUND OF THE INVENTION

Intervertebral disc degeneration (IVDD) is a common condition, affecting over 80 million adults in the United States alone, which can lead to debilitating neck and back pain. The intervertebral disc (IVD) structure consists of the collagen-heavy ring-shaped annulus fibrosus (AF) and the glycosaminoglycan (GAG)-rich nucleus pulposus (NP). The NP is vertically bound first via thin layers of hyaline cartilage and then by the vertebrae themselves. IVD resistance to external load is dependent on the hydrophilic GAG molecules that maintain IVD hydrostatic pressure. Moving caudally down the spine, the NP increases in volume to withstand greater loads which produce increased hydrostatic pressure within the IVD. While the exact etiology of disc degeneration remains unknown, depletion of GAGs in the NP is associated with IVD degeneration.

Over 25% of the U.S. adult population reports lower back pain. Earlier detection of intervertebral disc degradation could help reduce the number of people reporting lower back pain. In other words, earlier detection will facilitate earlier intervention, which will significantly improve the outcome for many individuals at risk for developing lower back pain. The development of a more sensitive IVD degradation detection method would enable earlier detection of intervertebral disc degradation. The present invention provides tools and methodologies to address this very important need.

SUMMARY OF THE INVENTION

Intervertebral disc degeneration (IVDD), resulting in the depletion of hydrophilic glycosaminoglycans (GAGs) located in the nucleus pulposus (NP), can lead to debilitating neck and back pain. Magnetic Resonance Imaging (MRI) is a promising means of IVD assessment due to the correlation between GAG content and MRI relaxation values. Furthermore, anomalous (i.e. non-monoexponential) relaxation models have yielded higher sensitivity to specific matrix components compared to conventional monoexponential models. Here, $T_{1\rho}$ and $T_2$ relaxation data were obtained from healthy cervical IVDs, and relaxation data was modeled using both conventional and stretched exponential (SE) decays. Normalized histograms of the resultant quantitative MRI (qMRI) maps were fit with stable distributions. SE models fit relaxation behavior with lower error compared to monoexponential models, indicating anomalous relaxation behavior in healthy IVDs. SE model parameters $T_{1\rho}$ and $\alpha_{T1\rho}$ increased with IVD segment, while conventional monoexponential measures did not vary. The improved model fit and correlation between both SE $T_{1\rho}$ and $\alpha_{T1\rho}$ with IVD level indicates that these parameters are more sensitive biomarkers for detection of GAG content variation.

A stretched exponential (SE) function was used to model T2 relaxation in cartilage, which associated the stretching parameter $\alpha$ with GAG content in situ, and demonstrated improved specificity to GAG over monoexponential relaxation values. Here, we present observations of the SE decay model of T1ρ in vivo in the context of IVD composition.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
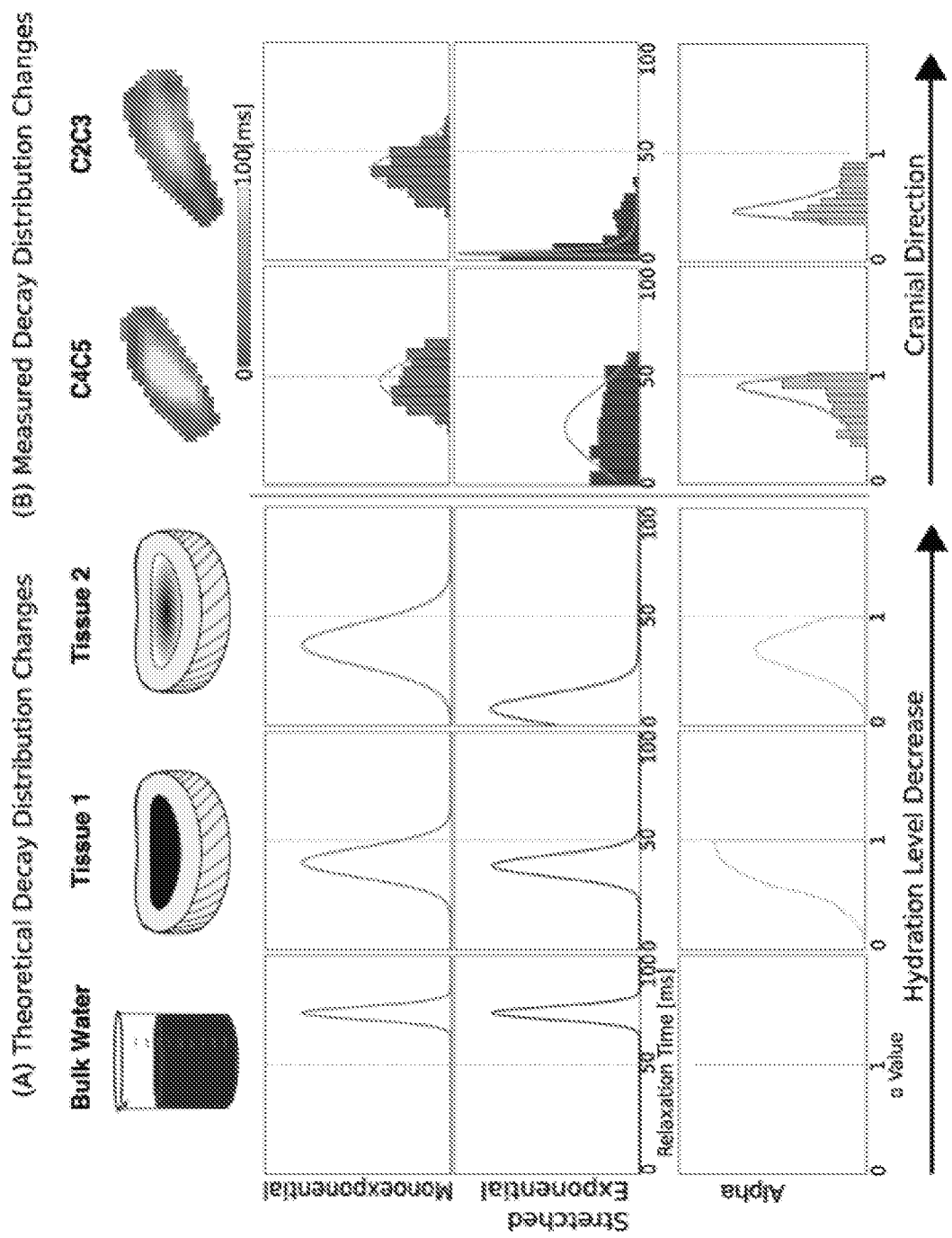
FIG. 1 is a set of images and graphs depicting that shifts in the distribution of relaxometry times are larger in the stretched exponential (SE) compared to the monoexponential (ME) model, both theoretically and experimentally. (A) The monoexponential and SE models do not differ for the bulk water case (with $\alpha$ values all being one). Adding complexity to the sample (i.e. changing from bulk water to IVD) lowers the relaxation values and decreasing hydration lowers these values more still. The addition of the $\alpha$ term allows for a higher dynamic range, shown here as the change in the peak of the distributions, allowing for higher sensitivity to compositional differences. (B) The greater difference in relaxometry distribution between discs for the SE model highlights the fact that intervertebral disc hydration increases caudally.

Magnetic Resonance Imaging (MRI) is a promising tool for IVD assessment. GAG deficiencies are routinely assessed in the research setting using histology. However, it has long been a goal of medicine to detect early soft tissue degeneration in vivo. MRI is an ideal modality for early detection of IVDD in vivo due to its excellent noninvasive soft tissue contrast and routine clinical use. Furthermore, the ability of MRI to provide enhanced tissue characterization through quantitative relaxometry sets it apart as a diagnostic tool. In a comparable tissue, $T_2$ relaxation analysis has been heavily utilized for in vivo cartilage assessment due to its sensitivity to collagen and water content. In contrast, while $T_2$ values in the IVD have primarily been shown to be sensitive to water content, $T_{1\rho}$ values have been shown to be sensitive to GAG content.

While conventional relaxometry measures are helpful tools for detection of IVDD, monoexponential $T_2$ and $T_{1\rho}$ values have shown limited specificity to individual matrix components. Anomalous relaxation has been observed in similar biological systems with non-monoexponential signal models showing additional tissue composition information. The stretched exponential (SE) function has been used widely for modeling biological and physical phenomenon. An SE function was used to model $T_2$ relaxation data of bovine nasal cartilage, resulting in improved decay fitting and associating the stretching parameter α with GAG content in situ, suggesting an improved specificity to GAG content over conventional relaxation values. Therefore, a stretched exponential (SE) relaxometry model shows promise for improved IVDD composition and assessment.

Here we explore the use of the SE model to investigate healthy subject IVDs in vivo. Both conventional and SE models were applied to both $T_2$ and $T_{1\rho}$ relaxation data. Ultimately, we show a wider dynamic range in SE $T_{1\rho}$ model parameters across disc level, suggesting greater sensitivity to known level-wise compositional variations between IVDs compared to conventional in vivo measures. These sensitivity increases could lead to improved imaging biomarkers, allowing for detection of subtle tissue composition changes such as those found in early IVDD.

Relaxation Models

The SE model for fitting transverse magnetization ($T_2$) decay profiles has previously been derived [Reiter D A, Magin R L, Li W, Trujillo J J, Pilar Velasco M, Spencer R G. Anomalous T2 relaxation in normal and degraded cartilage. Magn. Reson. Med. 2016; 76:953-962 doi: 10.1002/mrm.25913; Magin R L, Li W, Pilar Velasco M, et al. Anomalous NMR relaxation in cartilage matrix components and native cartilage: fractional-order models. J. Magn. Reson. 2011; 210:184-91 doi: 10.1016/j.jmr.2011.03.006]. The conventional monoexponential $T_2$ relaxation decay equation is written as:

$$M_{xy}(t) = M_0 e^{-TE/T_2} \quad [1]$$

Where $M_{xy}$ is the transverse magnetization, $M_0$ is the initial magnetization, $T_2$ is the calculated time constant, and TE is the echo time. The stretched exponential decay equation is written as:

$$M_{xy}(t) = M_0 e^{-(TE/T_{2se})^\alpha} \quad [2]$$

where the stretching parameter, α, allows for the modeling of broad continuous distributions of relaxation times suitable for capturing varying degrees of tissue microstructural complexity.

$T_2$ relaxation times in complex tissues can depend on the selection of interpulse delays due to a variety of effects (e.g. diffusion through field inhomogeneities and spin-spin coupling). The influence of these effects, which result in varying degrees of spin dephasing, can be minimized by using a sufficiently short interpulse delay. In the limit of vanishing interpulse delay time relative to pulse length, magnetization is effectively locked in the rotating frame, and $T_2$ relaxation approaches the spin-lattice relaxation time in the rotating frame, $T_{1\rho}$. Through varying the application of the spin-lock pulse frequency, relaxation in the rotating frame can be measured over a wide range of frequencies below the Larmor frequency, permitting the observation of interactions between water and extracellular matrix molecules (i.e. exchange of protons between mobile matrix proteins and water). As $T_2$ and $T_{1\rho}$ probe similar motional properties, and $T_2$ has shown anomalous decay in IVDs, it is hypothesized that $T_{1\rho}$ may also exhibit anomalous decay. The conventional model for monoexponential $T_{1\rho}$ relaxation is written as:

$$M_{xy}(TSL) = M_0 e^{-TSL/T_{1\rho}} \quad [3]$$

where TSL is the duration of the spin lock pulse. Similar to equation 2, the stretched exponential $T_{1\rho}$ relaxation model is written as:

$$M_{xy}(TSL) = M_0 e^{-(TSL/T_{1\rho SE})^\alpha} \quad [4]$$

Using equations 1-4, two different models (conventional and SE) for spin-spin and spin lattice relaxation in the rotating frame ($T_2$ and $T_{1\rho}$) yield 6 different model parameters to analyze: $T_{2Mono}$, $T_{2SE}$, $\alpha_{T2}$, $T_{1\rho Mono}$, $T_{1\rho SE}$, and $\alpha_{T1\rho}$.

A graphical representation of the expected behavior of these models is shown in FIG. 1, where the limiting case of bulk water produces a monoexponential decay with $\alpha=1$. Theoretical distributions of monoexponential and stretched exponential relaxation parameters are shown for IVD tissues with different hydration levels, where additional matrix components to the sample (i.e. a tissue vs bulk water) are expected to lead to anomalous relaxation that is better represented by the SE model.

Example 1

Materials and Methods

Raw Data Acquisition and Processing

Cervical IVDs (C2C3-C6C7) were imaged in 15 healthy subjects (7/8 males/females; average age=24.7) using a 3T GE MRI scanner. A magnetization-prepared angle-modulated partitioned k-space spoiled gradient echo snapshots (MAPSS) $T_{1\rho}$ sequence was acquired with the following parameters: spin lock power: 500 Hz spin lock times: [1, 5, 20, 40, 60] ms [Li X, Wyatt C, Rivoire J, et al. Simultaneous acquisition of T1ρ and T2 quantification in knee cartilage: Repeatability and diurnal variation. *J. Magn. Reson. Imaging* 2014; 39:1287-1293 doi: 10.1002/jmri.24253]. A $T_2$ sequence was also acquired (echo times: [6.78, 13.97, 21.15, 42.72] ms). Shared imaging sequence parameters were: FOV: 14 cm, matrix: 256×128, slice thickness: 4 mm, views per segment: 64, TR 1.2 s, number of slices: 26, ARC acceleration factor: 2, number of signal averages: 4.

Figure 2:
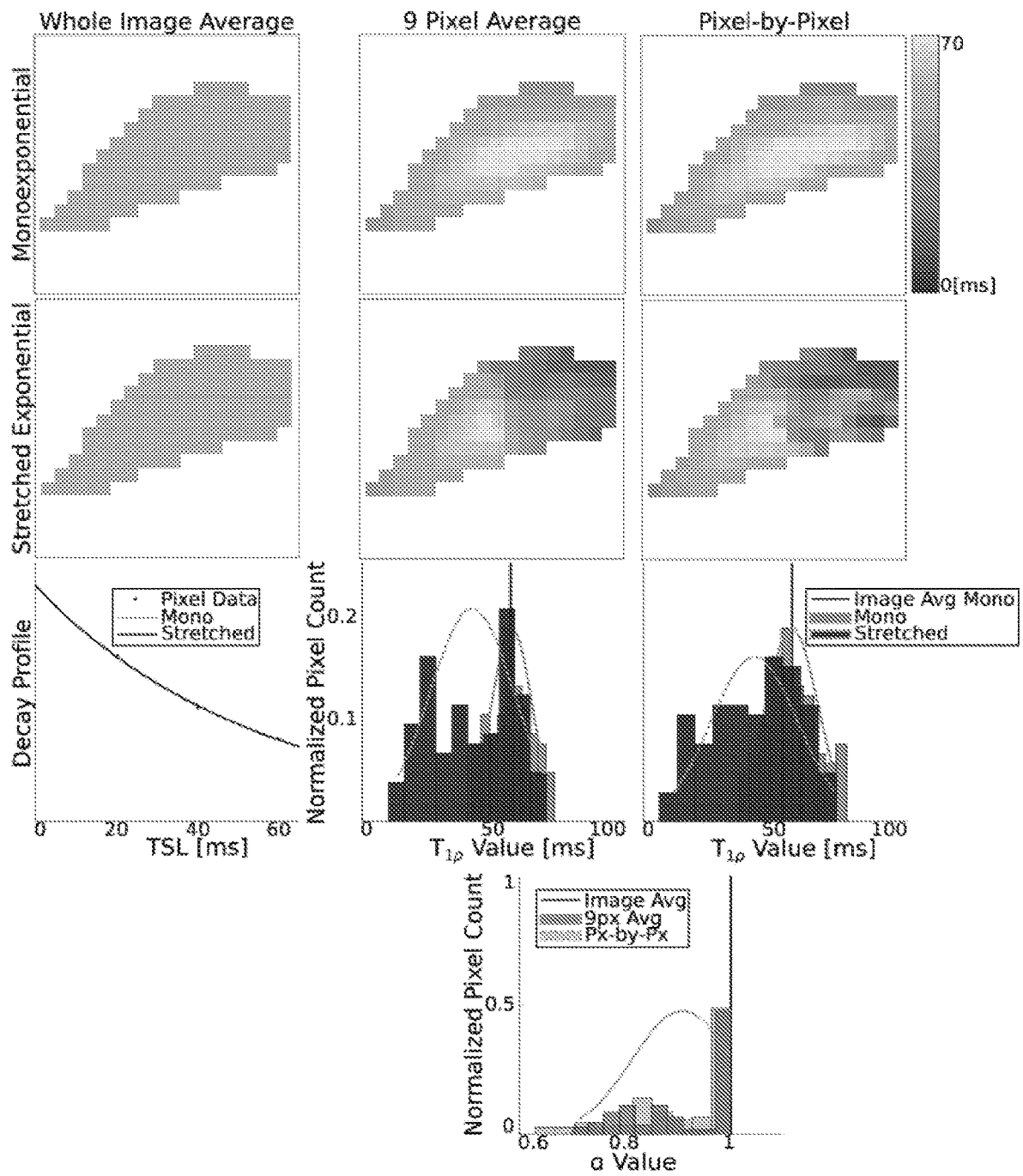
FIG. 2 is a set of graphs showing a reliable pixel-by-pixel processing method, allowing for maximum spatial information retention while minimizing noise. Evaluating the entire disc as a single pixel (by averaging all values at each time point) is not a spatially sensitive diagnostic tool, yet it provides an excellent baseline for measuring other processing methods due to its inherent noise minimization. Whole image $T_{1\rho}$ averages for monoexponential and SE models are 56.4 ms and 49.6 ms respectively. The 9-pixel moving window average allows for increased spatial information with $T_{1\rho}$ $\delta$ values of 56.8 ms and 41.7 ms for monoexponential and SE respectively. However, the pixel-by-pixel method was chosen for analysis because it minimizes noise as is evidenced by its $T_{1\rho}$ $\delta$ values (Monoexponential: 56.3 ms SE: 42.0 ms) being closer to that of the whole image average than the 9-pixel method. Not only does the pixel-by-pixel method have a minimal level of noise but it retains a higher level of spatial detail as well.
Figure 3:
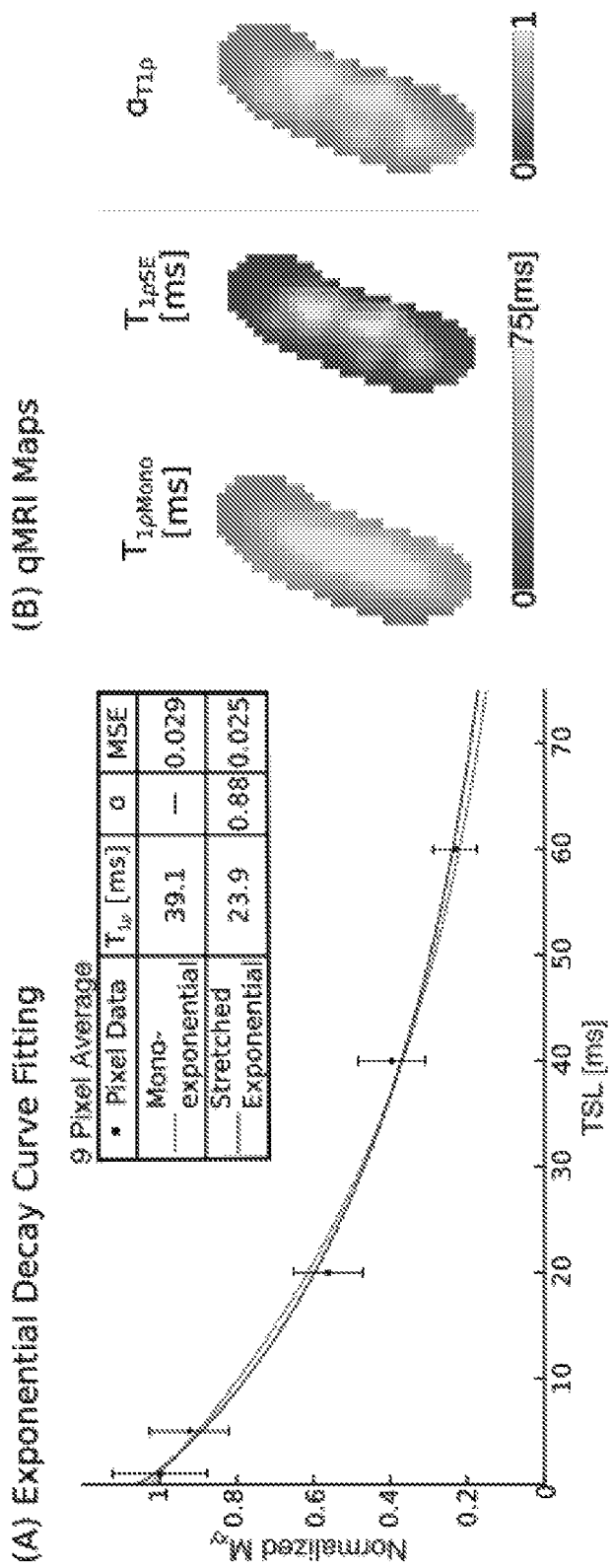
FIG. 3 is a pair of graphs illustrating that the exponential decay curve model fit reveals an increase in spatial heterogeneity for the stretched exponential $T_{1\rho}$ and $\alpha_{T1\rho}$ compared to conventional $T_{1\rho}$. (A) The decay curves (a 9-pixel average is shown here for clarity) are qualitatively similar, yet the resulting $T_{1\rho}$ values for both models are drastically different. The inclusion of the $\alpha$ value results in a significantly smaller MSE ($p<0.01$). (B) Higher levels of detail are visible in the $T_{1\rho}$ SE and $\alpha$ maps compared to the monoexponential map. This sensitivity leads to increased sensitivity to matrix composition differences.

The first spin lock time (TSL) for the $T_{1\rho}$ relaxation data was excluded from relaxation fitting due to the substantial increase in mean squared error it produced for all models compared with removal of other data (MSE). Pixel-by-pixel processing was chosen for analysis because of its relatively low noise compared to other techniques (FIG. 2). Decay curve fitting for both the conventional and SE ($\alpha$ bounds: [0.4,1]) models were completed utilizing MATLAB's curve fitting toolbox (FIG. 3). Signal to Noise Ratios (SNRs) were calculated by comparing the average value of the whole disc signal to the mean of a background sample equal in pixels from the final TSL/TE of each disc. SNR was used as a crude method of comparison for determining a cutoff for exclusion. Discs with low SNR (<2) and pixel decays with an $R^2$ value <0.66 [Wirth W, Maschek S, Roemer F W, Eckstein F. Layer-specific femorotibial cartilage T2 relaxation time in knees with and without early knee osteoarthritis: Data from the Osteoarthritis Initiative (OAI). Nat. Publ. Gr. 2016 doi: 10.1038/srep34202] or with an outlier decay time (Grubb's Test, $\alpha=0.05$) were excluded from the study. Quantitative MRI (qMRI) maps of the outputs from conventional (i.e. $T_{2Mono}$ and $T_{1\rho Mono}$) and SE fits (i.e. $T_{2SE}$, $\alpha_{T2}$, $T_{1\rho SE}$, and $\alpha_{T1\rho}$) were created based on pixel-wise fitting (FIG. 3). The qMRI maps were smoothed with a locally weighted scatterplot smoothing (LOWESS) filter (span: 10 pixels) for noise and edge effect minimization [Chan D D, Cai L, Butz K D, et al. Functional MRI can detect changes in intratissue strains in a full thickness and critical sized ovine cartilage defect model. J. Biomech. 2018; 66:18-25 doi: 10.1016/J. JBIOMECH. 2017.10.031].

Region of Interest Analysis

Regions of interest (ROI) were manually segmented as binary masks containing the whole disc, AF, and NP using the $T_{1\rho}$ weighted image with the shortest TSL. To characterize differences in relaxation values of a tissue compartment, qMRI map histograms were created and normalized by the total number of pixels. To investigate potential differences between distributions of parameters between disc levels within a given tissue compartment, the histograms were fit with stable distributions with standard bounds ($\alpha=(0,2]$, $\beta=[-1,1]$, $\gamma=(0, \infty)$, $\delta=(-\infty,\infty)$) as the distributions were found to be non-normal (p>0.05). Analogous to the position of a normal distribution being represented by the distribution mean, the stable distribution position is represented by the $\delta$ value with $\alpha$ and $\beta$ representing the distribution symmetry and skewness, respectively.

To compare level-wise differences in model parameters, the resultant $\delta$ values of each stable distribution (monoexponential, SE and $\alpha$) were analyzed as a function of anatomical disc level. Each subject's IVD $\delta$ values were normalized by subtracting the lower fitting bound and then dividing by the full range of bounds and offsetting all IVDs for that subject by the C2C3 $\delta$ value:

$$\delta_{IVD} = ((\delta_{IVD} - LB)/(UB - LB)) - \delta_{C2C3} \quad [5]$$

Statistics

Model deviations were characterized by comparing the MSE of both models using a one-way analysis of variance (ANOVA). Histogram normality was assessed using Shapiro-Wilks test. Absolute intradisc differences were determined using Kruskal-Wallis test. The correlation between $\delta$ values and IVD level was evaluated using a Spearman's rank correlation coefficient testing for monotonic relationships. Statistical significance was set at p<0.05.

Example 2

Results

Figure 4:
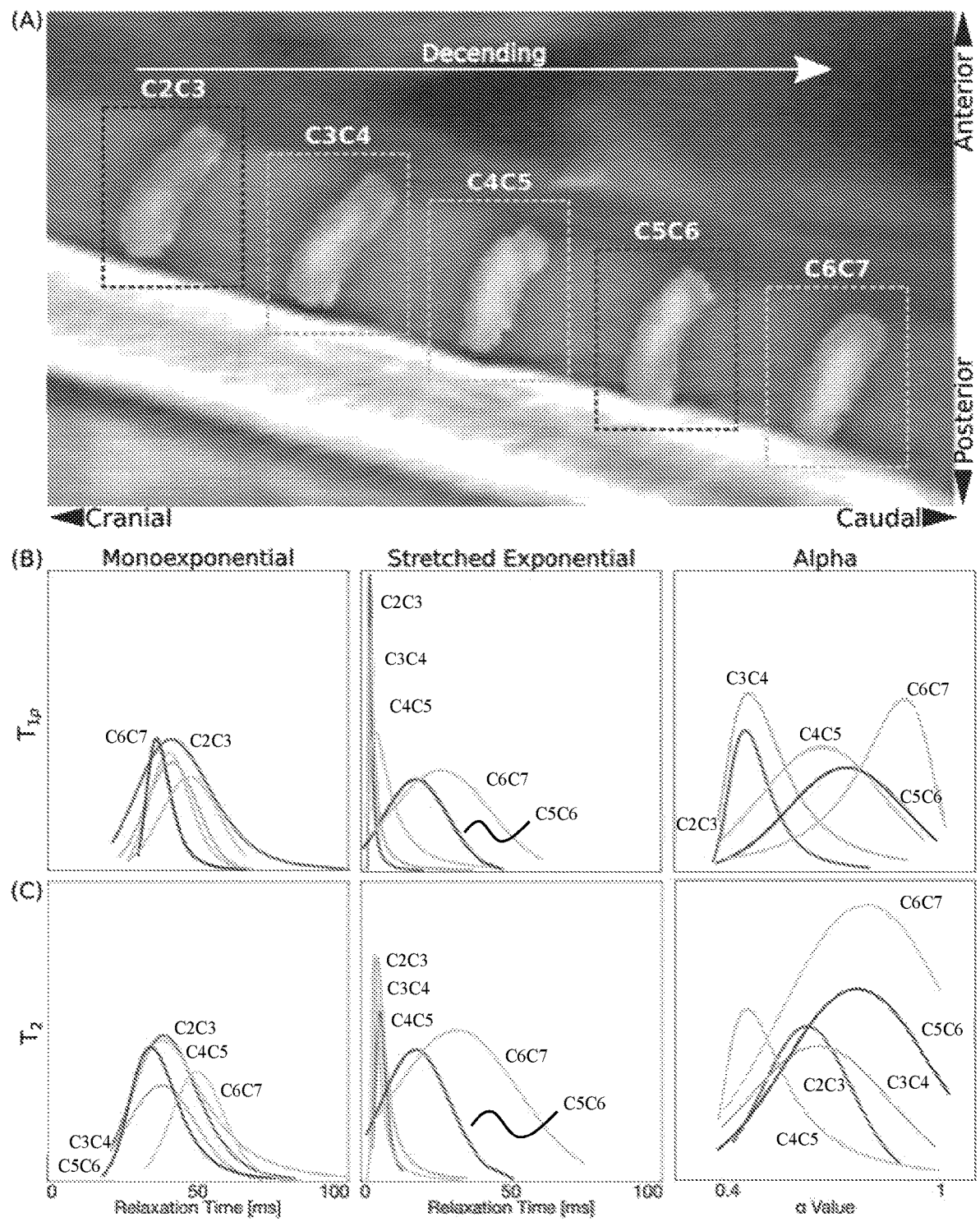
FIG. 4 is an image and a set of six (6) graphs. In a single subject, $T_{1\rho}$ and $T_2$ SE distribution peaks and corresponding α distribution peaks caudally increase with IVD segment, while the monoexponential distribution peaks show no positional relationship. (A) The qMRI maps, overlaid on an anatomical image (C2C3-C6C7), show the positional relationships of the discs. (B, C) The single subject $T_{1\rho}$ and $T_2$ stable distributions show a cranial-caudal relationship in the stretched exponential and alpha terms, while the monoexponential terms do not.
Figure 5A:
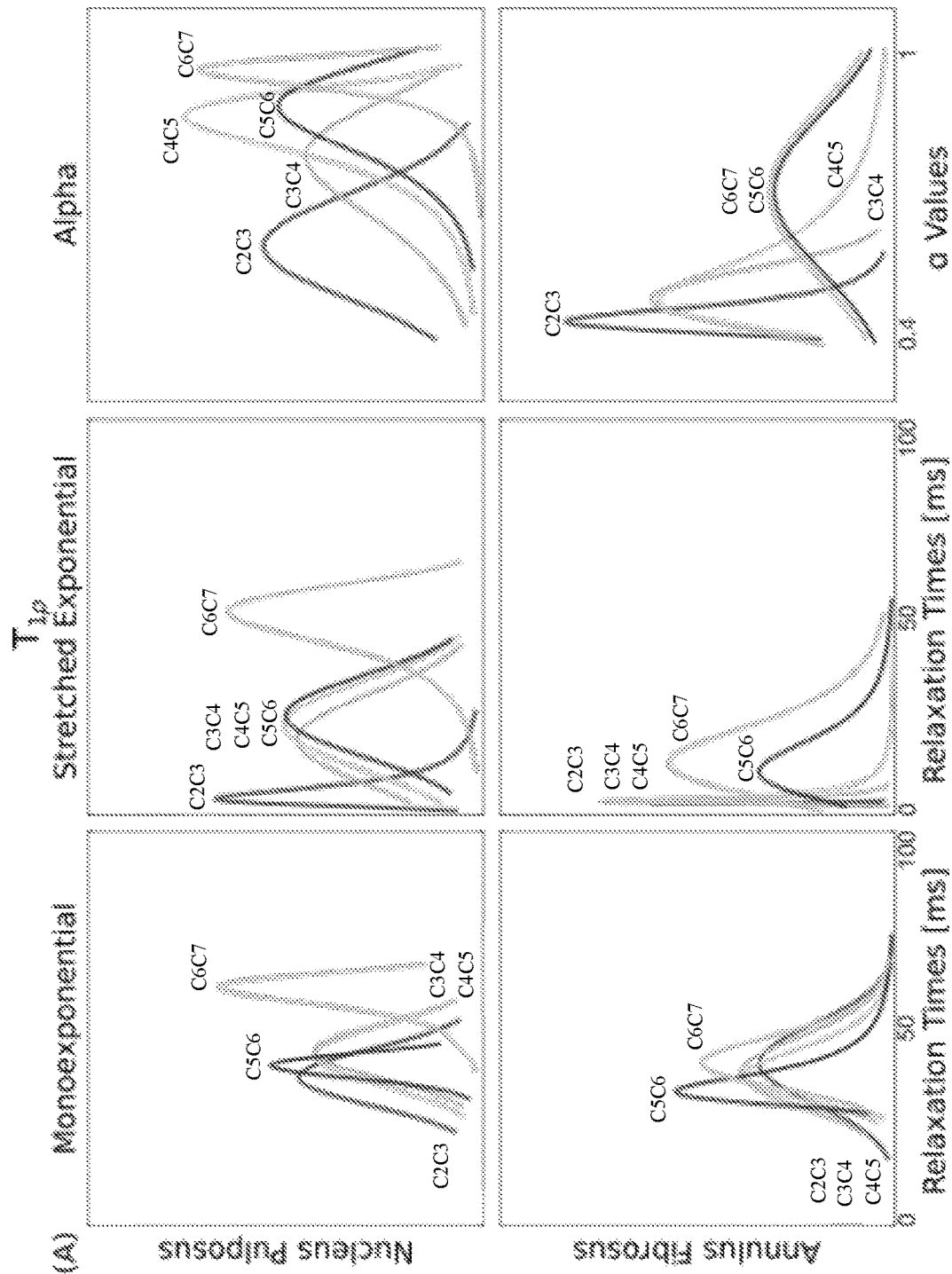
FIG. 5A is a set of six graphs. Single-subject nucleus pulposus $T_{1\rho}$ and $\alpha_{T1\rho}$ stable distributions show a strong qualitative correspondence with IVD level whereas all others do not. The $T_{1\rho}$ stable distributions show a caudally sensitive trend for the SE terms of the NP while monoexponential NP and all AF distributions do not show a trend.
Figure 5B:
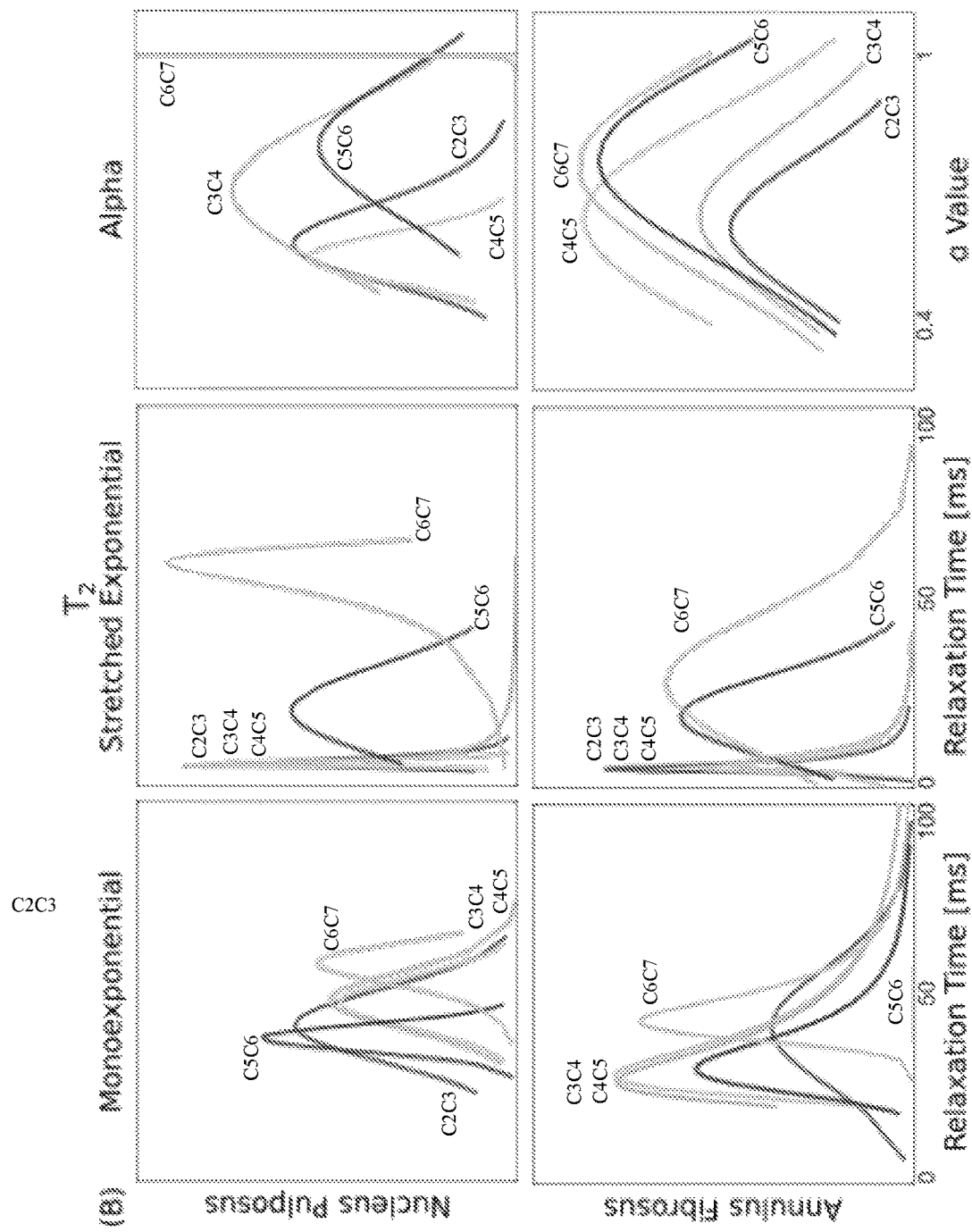
FIG. 5B is a set of six graphs. Single-subject nucleus pulposus $T_{1\rho}$ and $\alpha_{T1\rho}$ stable distributions show a strong qualitative correspondence with IVD level whereas all others do not. The $T_2$ stable distributions show no trend.

Single subject analysis shows level-wise increase in SE $T_2$ and $T_{1\rho}$ model parameters moving caudally with IVD segment based on the δ values from the disc-wise distributions, but monoexponential models found no qualitative differences (FIG. 4). MSEs derived from model fits were lower in the stretched exponential model than the conventional model for both $T_{1\rho}$ and $T_2$ (p<0.01). While the SE ($T_{1\rho SE}$ and $T_{2SE}$) δ values qualitatively increase caudally, a stronger relationship exists in the δ values of the α terms ($\alpha_{T1\rho}$, $\alpha_{T2}$). These qualitative observations follow similar trends in both relaxation measures. However, they are more prominent in the $T_{1\rho}$ parameters than $T_2$. The SE ($T_{1\rho SE}$, $\alpha T_{1\rho}$, $T_{2SE}$, and $\alpha T_2$) δ values increase at the lower discs (C5C6-C6C7), particularly in the NP compared to the AF (FIGS. 5A and 5B).

Figure 6A:
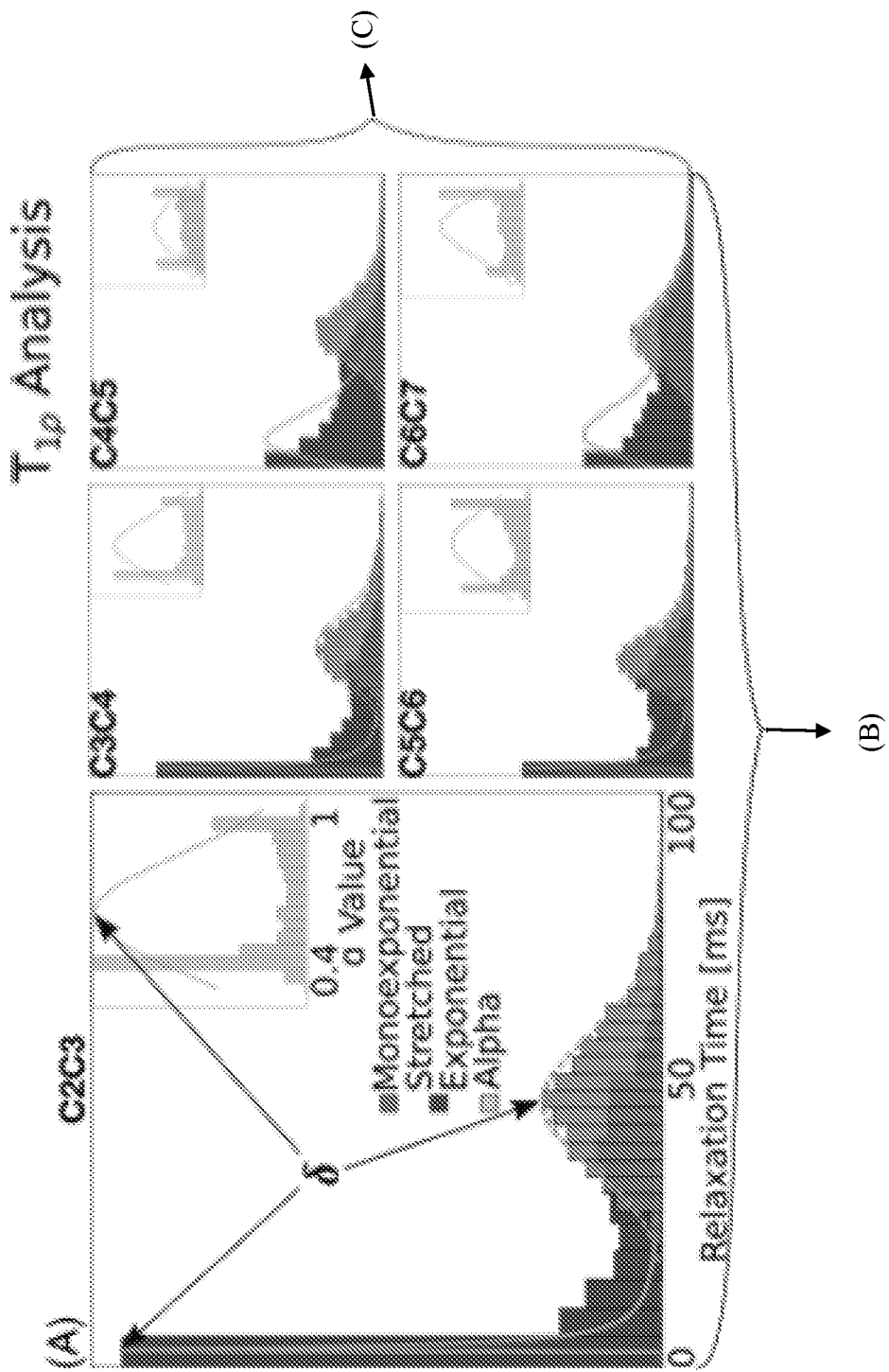
FIG. 6A is a set of five (5) graphs depicting that the $T_{1\rho}$ stable distribution analysis shows a significant monotonic increasing relationship between IVD level and peak values for the SE and α terms but not the monoexponential terms. The population-level (n=15) $T_{1\rho}$ stable distributions caudally increase. Arrows indicate the peak (δ) value of each distribution.

The population level (i) (n=15) $T_{1\rho}$ stable distribution analysis demonstrates a significant relationship between IVD level and SE model parameters (FIG. 6A). Caudally, the shape parameters (α (symmetry) and β (skewness) values of the stable distribution) and the δ value (peak location) of the $T_{1\rho Mono}$ data remain relatively constant while the $T_{1\rho SE}$ and $\alpha_{T1\rho}$ indicate level-wise dependence. $T_{1\rho SE}$ and $\alpha_{T1\rho}$ values in the NP vary dramatically as a function of location whereas the annulus data shows no level-wise dependence (FIG. 4B). The $T_{1\rho Mono}$ data has no discernable trend for each disc component. The whole disc normalized δ values (Eqn. 5) show statistically significant monotonic relationship between IVD level and parameters $T_{1\rho SE}$ and $\alpha T_{1\rho}$ (FIG. 4C) (Spearman's Correlations: p=0.03 and p=0.01 respectively). Both trends have similar correlation coefficients (ρ=0.29 for $T_{1\rho SE}$ and ρ=0.32 for $\alpha_{T1\rho}$) indicating similar disc level-wise sensitivity.

Figure 7A:
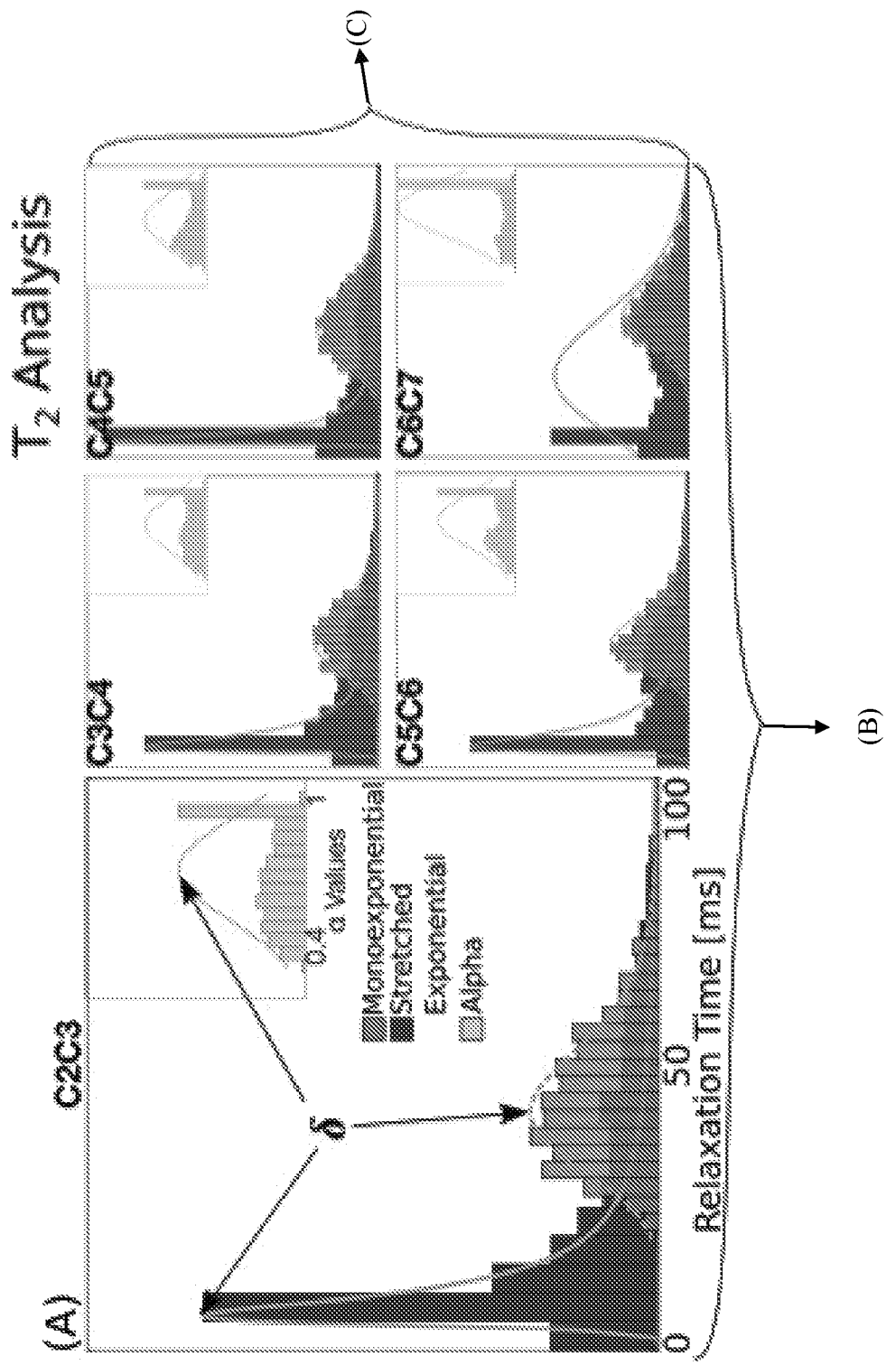
FIG. 7A is a set of five (5) graphs depicting that the $T_2$ stable distribution analysis shows no correlation between IVD level and any term. The population-level (n=15) $T_2$ stable distributions have no position-dependent correlation. Arrows indicate the peak (δ) value of each distribution.

The population level analysis of $T_2$ data shows no significant correlation between parameters ($T_{2Mono}$, $T_{2SE}$, and $\alpha_{T2}$) and IVD segment. All distributions remain relatively constant (FIG. 7A). No major differences were found per disc for each component (FIG. 5B). No correlation was found between location and $T_2$ values FIG. 5C) ($T_{2Mono}$: p=0.21, $T_{2SE}$: p=0.65, $\alpha_{T2}$: p=0.35).

This study was designed to evaluate the use of the SE fit in modeling healthy subject IVD MRI relaxometry in vivo. Both $T_2$ and $T_{1\rho}$ relaxation was investigated. $T_{1\rho SE}$ and $\alpha_{T1\rho}$ significantly correlate with disc level. Both monoexponential models and the SE $T_2$ model did not show any disc level dependence in these subjects.

The effectiveness of a stretched exponential model is dependent on two different phenomena: the presence of anomalous relaxation due to microscopic heterogeneity and the corresponding macroscopic change in decay time distributions. The monoexponential model was originally chosen to model bulk water which fit well due to the microscopic homogeneity of the sample [Bloch F. Nuclear Induction. Phys. Rev. 1946; 70:460-474 doi: 10.1103/Phys Rev. 70.460]. Therefore, when fitting both models to bulk water, the time constants for the monoexponential and SE models are expected to be equivalent (FIG. 1A) with an alpha value of one in the SE model indicating a lack of sample complexity. Theoretically, as sample composition increases in complexity from bulk water (i.e. adding components such as collagen and proteoglycans, decreasing the hydration level of the tissue), decay rates will become anomalous (and shorten due to matrix-water interactions).

The monoexponential model may not accurately represent the anomalous signal decay in complex materials. Therefore, the variation in monoexponential decay times may not reflect as large of a dynamic range as expected. The addition of the alpha parameter permits the SE decay model to capture this variation. The result of the SE model detecting the increase in heterogeneity is an increase in model dynamic range. Within a given tissue region consisting of multiple pixels, this increased relaxation parameter range can be characterized by a stable distribution detailing changes on the macroscopic level. Measured relaxometry distributions of $T_{1\rho SE}$ and $\alpha_{T1\rho}$ suggest higher sensitivity to the expected level-dependent IVD composition differences than $T_{1\rho Mono}$ (FIG. 1B).

The SE model has a significantly lower MSE (p<0.01) suggesting a non-monoexponential model is a more appropriate decay fit. Furthermore, the SE model can recover a monoexponential decay with an α fit value of 1 (FIG. 3A). The resulting SE qMRI maps show greater spatial heterogeneity compared to the monoexponential qMRI map (FIG. 3B). This texture increase indicates the SE parameters can serve as useful bio markers to detect differences in IVD composition.

Inspection of the stable distributions from a single subject highlights differences in model fits (FIG. 4). The whole disc $T_{1\rho Mono}$ and $T_{2Mono}$ show no discernable trend. The $T_{1\rho SE}$ and $T_{2SE}$ stable distributions begin to increase in the lower IVD's while the $\alpha T_{1\rho}$ and $\alpha T_2$ distributions indicate a level-wise association throughout, particularly for $\alpha T_{1\rho}$. Single subject component analysis (NP vs. AF) reflects greater level-wise shifts in the NP SE parameter distributions supporting the proposed theory (FIGS. 5A and 5B). The increase in SE parameters—most visible in the $T_{1\rho}$ analysis—reflected by the parameter distribution δ values with respect to IVD level may reflects the level-wise increase of GAG content in the NP.

Figure 6B:
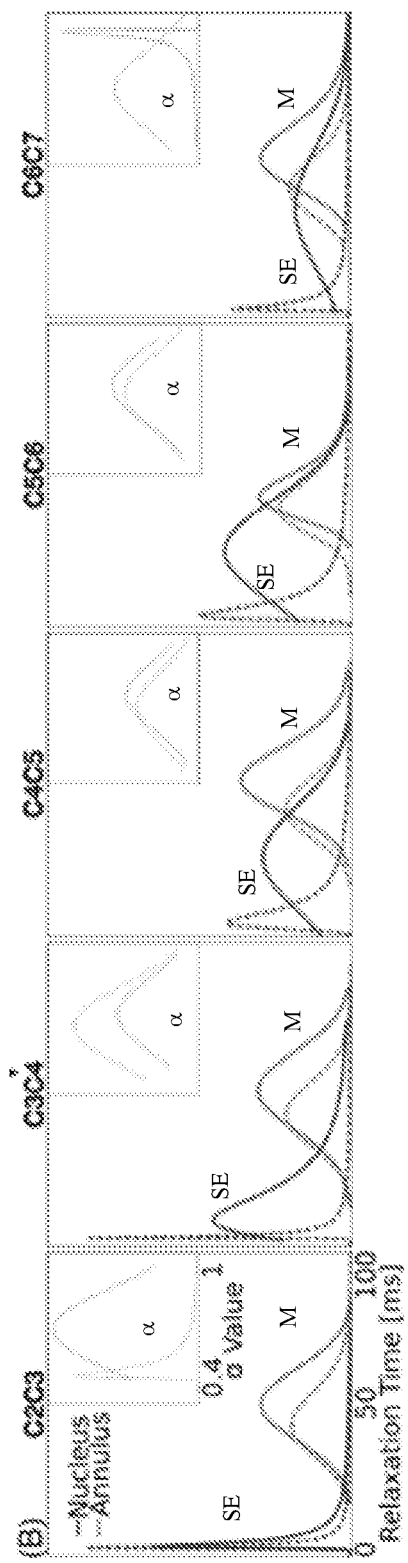
FIG. 6B is a set of five (5) graphs depicting that the $T_{1\rho}$ stable distribution analysis shows a significant monotonic increasing relationship between IVD level and peak values for the SE and α terms but not the monoexponential terms. Population-level analysis of the nucleus pulposus (NP) versus annulus fibrosus (AF) indicates a greater change in peak values for the NP compared to the AF.
Figure 6C:
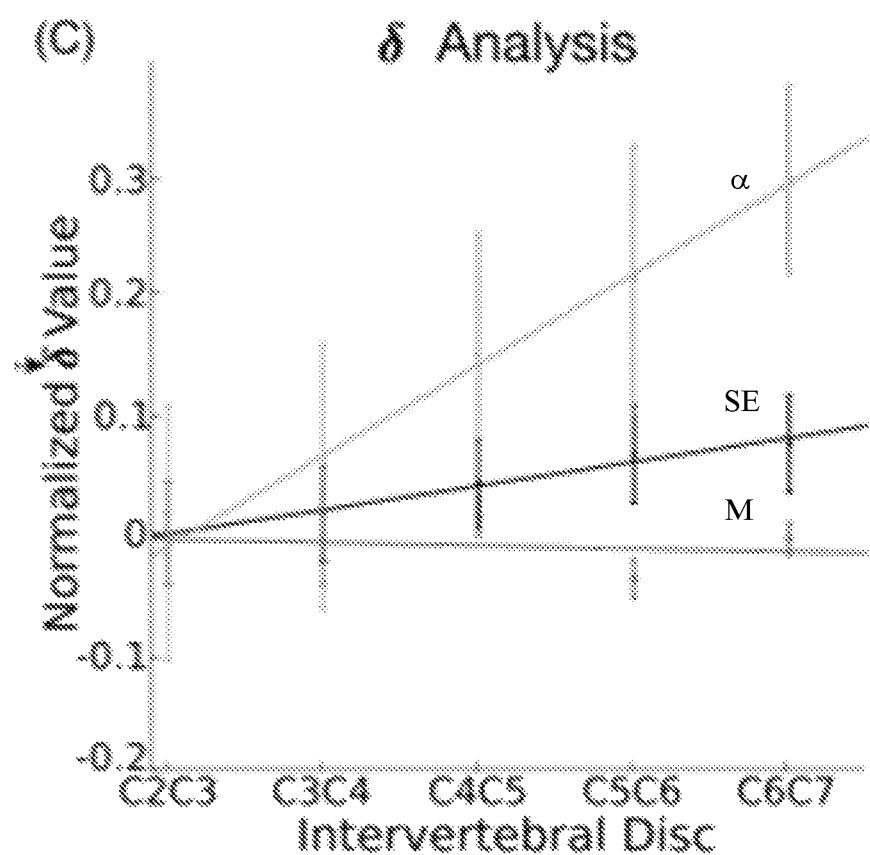
FIG. 6C is a graph depicting that the $T_{1\rho}$ stable distribution analysis shows a significant monotonic increasing relationship between IVD level and peak values for the SE and α terms but not the monoexponential terms. The Spearman's rank correlations of the normalized δ for $T_{1\rho}$ SE and α are significant (p=0.03 and p=0.01 respectively) and it is not significant for $T_{1\rho}$ monoexponential (p=0.58).

The population level $T_{1\rho}$ results are consistent with the hypothesis that δ values correlate with expected whole disc GAG content (FIGS. 6A-6C). The $T_{1\rho SE}$ and $\alpha_{T1\rho}$ stable distributions widen (changing the δ values) in the caudal direction, with the $\alpha_{T1\rho}$ being the more prominent of the two. A $T_{1\rho}$ component analysis shows a relationship between NP δ values and disc level indicating the NP is a major factor in distribution change (FIG. 6B). This supports a potential correlation between α values and NP microstructure. The normalized population level analysis of δ indicates a monotonic relationship with level for $T_{1\rho SE}$ and $\alpha T_{1\rho}$ ($T_{1\rho SE}$: p=0.03, $\alpha T_{1\rho}$: p=0.01, $T_{1\rho Mono}$: p=0.58) (FIG. 6C). Interestingly, the $T_{1\rho SE}$ and $\alpha_{T1\rho}$ terms are similar in sensitivity evidenced by their Spearman's rank correlation coefficients (ρ) $T_{1\rho SE}$: ρ=0.29, $\alpha_{T1\rho}$: ρ=0.32). While not intuitive, given the higher slope of the $\alpha_{T1\rho}$ values, the similarity can be explained when evaluating standard deviations. The α value range is smaller ([0.4,1]) than that of the $T_{1\rho}$ values ([0,100]). Therefore, while the $\alpha_{T1\rho}$ δ appears to be more sensitive due to the higher slope, the resultant higher standard deviation yields a sensitivity similar to the $T_{1\rho SE}$ δ fit. Ultimately, the δ analysis indicates that the SE model parameters may be more sensitive to compositional differences than previous methods.

Figure 7B:
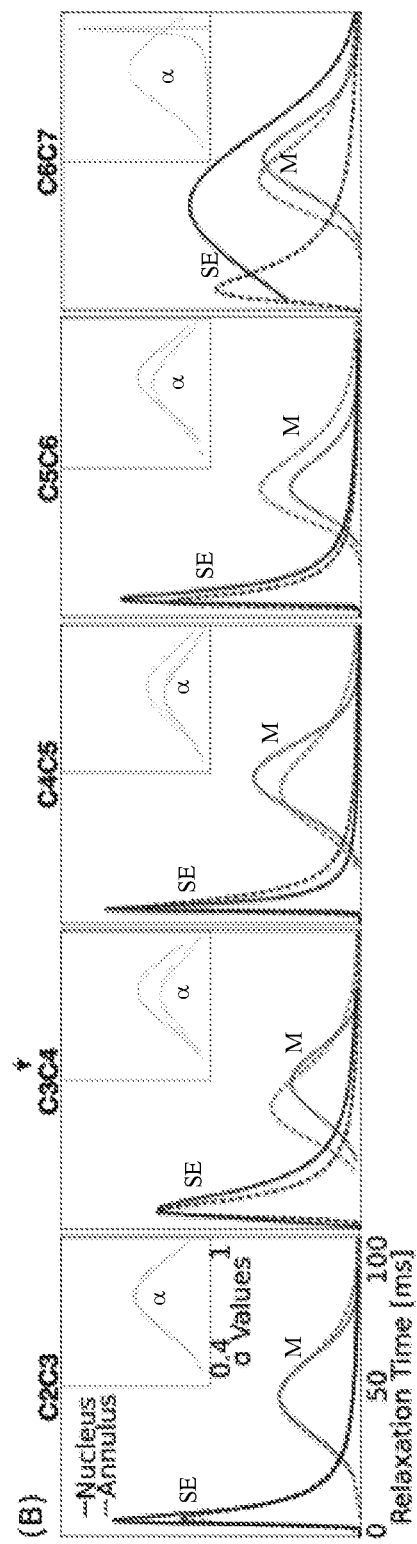
FIG. 7B is a set of five (5) graphs depicting that the $T_2$ stable distribution analysis shows no correlation between IVD level and any term. Population-level analysis of the nucleus pulposus (NP) versus annulus fibrosus (AF) indicates no detectable change in peak values for the NP compared to the AF.
Figure 7C:
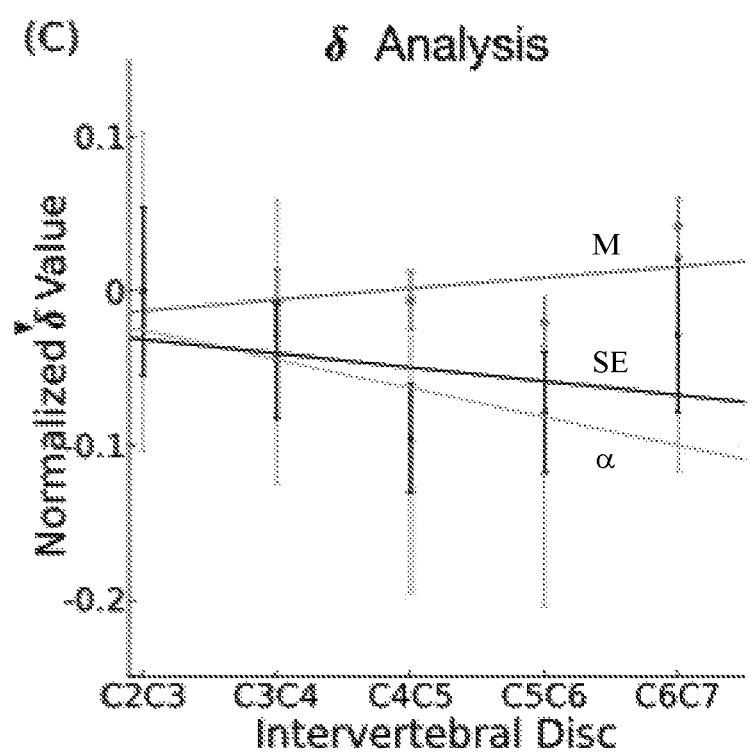
FIG. 7C is a graph depicting that the $T_2$ stable distribution analysis shows no correlation between IVD level and any term. The Spearman's rank correlations of the normalized δ values found no significance (monoexponential: p=0.21, SE: p=0.65, α: p=0.35).

The $T_2$ parameters show no significant correlation to IVD level (FIG. 7). The qualitative distribution changes that do exist are led by the NP differences. Although not significant, the $T_{2SE}$ and $\alpha_{T2}$ values show higher inter-IVD differences than $T_{2Mono}$. These findings indicate that $T_{1\rho}$ is a more sensitive method to investigate IVD compositional differences.

A stretched exponential model of $T_{1\rho}$ IVD relaxation yields more sensitive insights into IVD health. Current literature suggests a strong correlation between absolute GAG content, IVD health, and monoexponential $T_{1\rho}$ IVD relaxation. However, these in vivo approaches are typically at the population level (e.g. with cohorts greater than 15 participants (32-34)) and/or not IVD location specific (18), yielding limited utility at the individual patient level. A patient level correlation between relative IVD location and $T_{1\rho}$ values has never been demonstrated. The data presented here demonstrates this correlation thus indicating a before unknown measure of sensitivity which could prove useful in detecting finer IVD compositional changes, such as those present in early IVDD.

We observed no obvious level-wise variation in SE T2 model parameters in our healthy population. This may be due to the more limited acquisition parameters we used for in vivo imaging (e.g. echo times, signal quality, etc). Further studies can compare structural properties in model tissue systems with these relaxation model parameters to investigate their relationship to IVD function. Despite removing the first TSL, reliable exponential decay fits were achieved highlighting the reliability of the collected data. The overall dataset SNR is low, causing minor data exclusion. Disease oriented studies could investigate the efficacy of the SE fit for IVDD preclinical (animal) and clinical models in vivo.

Figure 8:
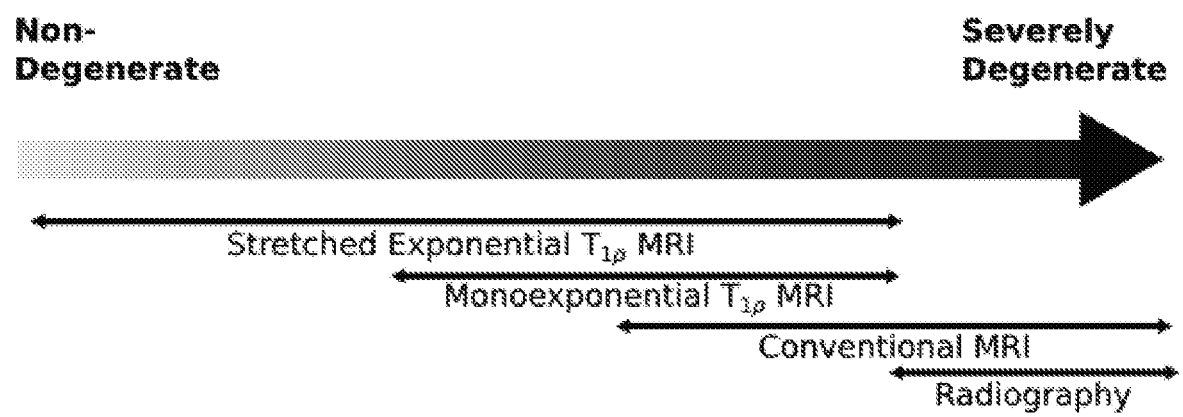
FIG. 8 is a graph depicting the larger dynamic range of the SE model compared to conventional methods which lead to earlier IVDD detection. The SE model's increased dynamic range allows higher sensitivity to compositional differences, detecting subtler IVD changes compared to conventional methods. The SE model will result in improved biomarkers for screening and early detection of IVDD.

The conventional monoexponential $T_{1\rho}$ decay model has been shown to correlate with GAG content. Additionally, $T_{1\rho}$ NP values decrease with disc degeneration. However, the conventional fit may provide a limited representation of the relaxation features available as they relate to important matrix-water interactions limiting standard relaxometry measures sensitivity to characterize IVD tissue status. Using a stretched exponential model with the addition of the α term will lead to improved sensitivity and possibly provide earlier detection of IVDD (FIG. 8). The parameter □ is thought to reflect a distribution of relaxation times and thus water mobility in the tissue microenvironment [Reiter D A, Magin R L, Li W, Trujillo J J, Pilar Velasco M, Spencer R G. Anomalous T2 relaxation in normal and degraded cartilage. Magn. Reson. Med. 2016; 76:953-962 doi: 10.1002/mrm.25913]. An increase in hydrostatic pressure with increasing caudal disc level is due to increased disc load [Schleich C, Müller-Lutz A, Zimmermann L, et al. Biochemical imaging of cervical intervertebral discs with glycosaminoglycan chemical exchange saturation transfer magnetic resonance imaging: feasibility and initial results. Skeletal Radiol, 2016; 45:79-85 doi: 10.1007/s00256-015-2251-0]. The $T_{1\rho SE}$ and $\alpha_{T1\rho}$ δ values indicate a monotonic relationship to these compositional changes (i.e. increased GAG content). The $T_{1\rho}$SE model is a more sensitive analytical method for IVD compositional difference detection than conventional models, holding promise as a biomarker for earlier IVDD detection.

One advantage of knowing IVD status would be increased sensitivity to IVD composition. When monitoring IVD health of a patient, a physician would have a more accurate understanding of the current situation. For instance, if the patient was bordering on having spinal fusion surgery, something that is often put off until necessary, it would help the physician make the right decision and feel more confident in their approach to treating the patient.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described.

What is claimed is:

1. A method for detecting intervertebral disc degeneration (IVDD) in a subject comprising the steps of:
   measuring a $T1_{\rho SE}$ relaxation time of glycosaminoglycan (GAG) in a disc of the subject using magnetic resonance imaging;
   comparing the measured $T1_{\rho SE}$ relaxation time to a baseline $T1_{\rho SE}$ relaxation time indicative of healthy tissue;
   measuring a $\alpha_{T1\rho}$ relaxation time of GAG in the disc of the subject using magnetic resonance imaging;
   comparing the determined $\alpha_{T1\rho}$ relaxation time to a baseline $\alpha_{T1\rho}$ relaxation time indicative of healthy tissue; and
   determining a decrease in the GAG content in the disc of the subject based on results of the comparing step for both the $T1_{\rho SE}$ relaxation time to a baseline $T1_{\rho SE}$ relaxation time and the $\alpha_{T1\rho}$ relaxation time to a baseline $\alpha_{T1}$ relaxation time, wherein a decrease in the GAG content in the disc of a subject is indicative of IVDD in the subject.

2. The method according to claim 1 wherein $T1_{\rho SE}$ relaxation time of GAG is measured in the nucleus pulposus (NP) of the subject using magnetic resonance imaging and wherein a decrease in the GAG content in the NP of a subject is indicative of IVDD in the subject.

3. The method according to claim 1 wherein the magnetic resonance imaging is processed using a pixel-by-pixel method.

4. A method of monitoring progress of intervertebral disc degeneration (IVDD) in a subject comprising the steps of:
   measuring a baseline $T1_{\rho SE}$ relaxation time of glycosaminoglycan (GAG) in a nucleus pulposus (NP) of a subject using magnetic resonance imaging;
   measuring one or more additional $T1_{\rho SE}$ relaxation times;
   comparing at least one of the one or more additional $T1_{\rho SE}$ relaxation times measured to the baseline value of the $T1_{\rho SE}$ relaxation time;
   measuring a baseline $\alpha_{T1\rho}$ relaxation time of GAG in the NP of the subject using magnetic resonance imaging;
   measuring one or more additional $\alpha_{T1\rho}$ relaxation times;
   comparing at least one of the one or more additional $\alpha_{T1\rho}$ relaxation times measured to the baseline value of the $\alpha_{T1\rho}$ relaxation time; and
   determining a decrease in the GAG content in the NP of the subject based on results of the comparing step for both the $T1_{\rho SE}$ relaxation time to a baseline $T1_{\rho SE}$ relaxation time and the $\alpha_{T1\rho}$ relaxation time to a baseline $\alpha_{T1}$ relaxation time, wherein a decrease in the GAG content in the NP of a subject is indicative of continued IVDD in the subject.

5. A method of evaluating the effectiveness of an intervertebral disc degeneration (IVDD) treatment comprising the steps of:
   measuring a baseline $T1_{\rho SE}$ relaxation time of glycosaminoglycan (GAG) in a nucleus pulposus (NP) of a subject prior to or upon initiation of the treatment using magnetic resonance imaging;
   measuring a baseline $\alpha_{T1\rho}$ relaxation time of the GAG in the NP of a subject prior to or upon initiation of the treatment using magnetic resonance imaging;
   initiating the treatment of the IVDD in the subject;
   measuring one or more additional $T1_{\rho SE}$ relaxation times after initiation of the treatment;

comparing at least one of the one or more additional $T1_{\rho SE}$ relaxation times measured after initiation of the treatment to the baseline value of the $T1_{\rho SE}$ relaxation time;

measuring one or more additional $\alpha_{T1_\rho}$ relaxation times after initiation of the treatment;

comparing at least one of the one or more additional $\alpha_{T1_\rho}$ relaxation times measured after initiation of the treatment to the baseline value of the $\alpha_{T1_\rho}$ relaxation time; and determining a change in the GAG content in the NP of the subject based on results of the comparing step for both the $T1_{\rho SE}$ relaxation time to a baseline $T1_{\rho SE}$ relaxation time and the $\alpha_{T1_\rho}$ relaxation time to a baseline $\alpha_{T1}$ relaxation time, wherein an increase in GAG content is indicative of treatment effectiveness.

6. The method according to claim 5 wherein the magnetic resonance imaging is processed using a pixel-by-pixel method.

7. A method for detecting intervertebral disc degeneration (IVDD) in a subject comprising the steps of:
measuring a $\alpha_{T1_\rho}$ relaxation time of glycosaminoglycan (GAG) in a disc of the subject using magnetic resonance imaging;
comparing the measured $\alpha_{T1_\rho}$ relaxation time to a baseline $T1_{\rho SE}$ relaxation time indicative of healthy tissue; and
determining a decrease in the GAG content in the disc of the subject based on results of the comparing step, wherein a decrease in the GAG content in the disc of a subject is indicative of IVDD in the subject.

8. A method for detecting intervertebral disc degeneration (IVDD) in a subject comprising the steps of:
measuring a $\alpha_{T1_\rho}$ relaxation time of glycosaminoglycan (GAG) in a nucleus pulposus (NP) of the subject using magnetic resonance imaging;
comparing the determined $\alpha_{T1_\rho}$ relaxation time to a baseline $\alpha_{T1_\rho}$ relaxation time indicative of healthy tissue; and
determining a decrease in the GAG content in the NP of the subject based on results of the comparing step, wherein a decrease in the GAG content in the NP of a subject is indicative of IVDD in the subject.

9. The method according to claim 8 wherein the magnetic resonance imaging is processed using a pixel-by-pixel method.

10. A method of monitoring progress of intervertebral disc degeneration (IVDD) in a subject comprising the steps of:
measuring a baseline $\alpha_{T1_\rho}$ relaxation time of glycosaminoglycan (GAG) in a nucleus pulposus (NP) of a subject using magnetic resonance imaging;
measuring one or more additional $\alpha_{T1_\rho}$ relaxation times;
comparing at least one of the one or more additional $\alpha_{T1_\rho}$ relaxation times measured to the baseline value of the $\alpha_{T1_\rho}$ relaxation time; and
determining progress of intervertebral disc degeneration based on results of said comparing step.

11. A method of evaluating the effectiveness of an intervertebral disc degeneration (IVDD) treatment comprising the steps of:
measuring a baseline $\alpha_{T1_\rho}$ relaxation time of glycosaminoglycan (GAG) in a nucleus pulposus (NP) of a subject prior to or upon initiation of the treatment using magnetic resonance imaging;
initiating the treatment of the IVDD in the subject;
measuring one or more additional $\alpha_{T1_\rho}$ relaxation times after initiation of the treatment;
comparing at least one of the one or more additional $\alpha_{T1_\rho}$ relaxation times measured after initiation of the treatment to the baseline value of the $\alpha_{T1_\rho}$ relaxation time; and
determining an effectiveness of the treatment based on results of the comparing step.

12. The method according to claim 11 wherein the magnetic resonance imaging is processed using a pixel-by-pixel method.

* * * * *